US006673378B1

(12) United States Patent
Fritz

(10) Patent No.: US 6,673,378 B1
(45) Date of Patent: Jan. 6, 2004

(54) PHOSPHATIDYLSERINE-CONTAINING MUSCLE DEVELOPMENT DIET SUPPLEMENT AND ANTI-CATABOLIC DIETARY NUTRIENTS

(76) Inventor: Robert Fritz, 1346 Highland Ave., Martinez, CA (US) 94553

( * ) Notice: Subject to any disclaimer, the term of this patent is extended or adjusted under 35 U.S.C. 154(b) by 0 days.

(21) Appl. No.: 08/551,326

(22) Filed: Nov. 1, 1995

(51) Int. Cl.[7] .............................. A61K 35/78; A23L 1/30
(52) U.S. Cl. ........................... 424/757; 424/725; 514/2; 514/23; 514/76; 426/601; 426/648; 426/656; 426/658; 426/662
(58) Field of Search .............................. 424/195.1, 725, 424/757; 514/2, 23, 76; 426/601, 648, 656, 658, 662

(56) References Cited

U.S. PATENT DOCUMENTS 4,874,553 A * 10/1989 Hager, Jorg et al. ........ 260/403
5,260,219 A * 11/1993 Fritz ........................... 436/71

OTHER PUBLICATIONS

Product Alert, Jan. 8th, Solgar Gold Label Supplement Phosphatidyl Serine Complex, 1995.*
Williams, In Oxford Textbook of Sports Medicine, Ed. Harries, Williams, Stanish, and Micheli, Chapter 1.2.2, pp. 65–81, 1994.*
Alekseeva et al, Farmatsiya (Mosc), 28:51–53, English translation of abstract only, 1979.*
Guyton, Human Physiology And Mechanisms Of Diseases, 4th Ed., W.B. Saunders Co., pp. 585–594, 1987.*
Katiyar et al., Nutrient composition of Nikku muth, a traditional soybean cultivar of Kashmir Valley, with particular reference to content of lipids and proteins, Food Chem., vol. 32, pp. 117–123, 1989.*
Sapse, Alfred T., "Cortisol as the Cause of –Stress– Diseases," *Rejuvenation*, vol. XII, No. 3–4, p. 31–36, Sep. 1984.
Austad, Stephen, "Stressed to Kill," *Natural History*, p. 66–68, Jan. 1995.
Lebow, Franca, "'100% Successful' Anorexia Rx Suspect— Findings Unreplicated," *Medical Tribune*, p. 5, Sep. 19, 1984.
Rizza, Robert A., et al, "Cortisol—Induced Insulin Resistance in Man: Impaired Suppression of Glucose Production and Stimulation of Glucose Utilization Due to a Postreceptor Defect of Insulin Action*," *Journal of Clinical Endocrinology and Metabolism*, vol. 54, No. 1, p. 131–138 (1982).
Monteleone, Palmiero, et al, Effects of Phosphatidylserine on the Neuroendocrine Response to Physical Stress in Humans, *Neuroendocrinology*, vol. 52, p. 243–248 (1990).
Monteleone, Palmiero, et al, "Blunting by Chronic Phosphatidylserine Administration of the Stress–Induced Activation of the Hypothalamo–Pituitary–Adrenal Axis in Healthy Men," *European Journal of Clinical Pharmacology*, vol. 42, p. 385–388 (1992).
Dr. Pfister, Th., "Acute Oral Toxicity Study with Phosphatidylserine Food Grade in Rats," *Lucas Meyer Sponsored Report*, Jul. 12, 1995.
Lucas Meyer, Inc. "Corti–PS 20F," Aug. 1995.

* cited by examiner

Primary Examiner—Christopher R. Tate
(74) Attorney, Agent, or Firm—Richard Esty Peterson

(57) ABSTRACT

An anti-catabolic dietary supplement, phosphatidylserine, and diet and exercise programs using phosphatidylserine for lean muscle development and optimized conditioning.

8 Claims, 1 Drawing Sheet

PS INTAKE PROTOCOL
FACTORS- In Total Mg/Day

| Reference Range | <200 lb | >200 lb | Over 5 Hours of Workouts/ Week | Dieting | Extra Emotional Stress | Load Cycle |
|---|---|---|---|---|---|---|
| Physical Training | 300 | 400 | 500 | 600 | 700 | 800 |
| Dieting | 200 | 300 | 400 | N/A | 550 | N/A |
| Health-Wellness | 100 | 200 | 300 | 400 | 500 | N/A |

FIG. 1

PHOSPHATIDYLSERINE-CONTAINING MUSCLE DEVELOPMENT DIET SUPPLEMENT AND ANTI-CATABOLIC DIETARY NUTRIENTS

BACKGROUND OF THE INVENTION

This invention relates to a natural food supplement, phosphatidylserine, to inhibit protein catabolism and promote health and fitness in animals and humans. In particular, this natural, soy derived supplement is preferably used in a regime in which the body is intentionally stressed by dieting or physical exercise. Under such conditions, a program for controlled intake of phosphatidylserine, a constituent in a composition of natural soy phospholipids, suppresses the release of excess cortisol resulting from the physical stress of exercise or dieting.

Optimal health and fitness depends on a combination of diet and exercise. Where the general objective of a health regimen is to achieve physical well-being and avoidance of sickness, a variety of factors must be considered. Typically, health advocates agree that the combination of a balanced diet and moderate exercise is the key to good health. This oversimplification does not account for the wide variations in activity that affect an optimized health regimen.

For example, dieting by restricting food intake without exercise is generally considered unwise. However, if the objective is weight loss without muscle loss, exercise is encouraged and dietary considerations, to maintain necessary dietary minimums, become complex. The body is stressed both by limited food intake and the physical trauma of exercise.

If the objective is increased body strength and muscle mass, the body may encounter extreme physical stress from systematic physical training trauma and a substantially increased food intake. To avoid fatigue and accumulation of fat instead of muscle, the timing and content of food intake relative to the exercise program must be regimentally controlled.

The foregoing two extremes represent the type of induced physical stress for which a programmed regime for use of the dietary supplement, soy derived phosphatidylserine, is directed. In both extremes, the objective is to inhibit protein catabolism and encourage metabolism of dietary and stored carbohydrates and especially body fat for energy.

In U.S. Pat. No. 5,260,219, issued Nov. 9, 1993 to this inventor, entitled, "METHOD OF DETERMINING NITROGEN BALANCE AND FAT LOSS FOR PERSONS INVOLVED IN DIET AND/OR PHYSICAL TRAINING PROGRAM," a simple system and self test kit for determining urea nitrogen and ketone concentrations in a urine stream was described. The system enabled a user to determine his or her protein nitrogen turnover and body fat metabolism in order to design an effective dietary and exercise program. The teachings of this patent are incorporated herein by reference. The patent teaches the general type of regimen for a weight loss diet or a physical training program that is contemplated for effective use of the phosphatidylserine supplement here described. It is to be understood that the use of phosphatidylserine as a dietary supplement is best used in conjunction with a program or regime involving controlled intake of a protein supplement. Use of a protein supplement, however, is not required. The contemporaneous intake of dietary protein to insure an anabolic state is advantageous for optimum results when taking soy derived, phosphatidylserine supplement.

The basic problem with a haphazard weight loss diet or intermittent strenuous physical activity is the body's response by elevating the level of production of cortisol. Elevated cortisol is an indiscriminate metabolic/catabolic agent that breaks down the body's protein, including muscle tissue, into amino acids which are converted into glucose in the liver. Elevated cortisol is therefore counterproductive in both described situations of diet and exercise where high cost protein is metabolized into cheap sugar fuels. In dieting, desirable muscle is broken down along with stored fat, and in strenuous exercise, hard earned muscle is cannibalized leaving the body weak and exhausted. In both the case of diet and exercise, the induced physical stress results in the triggering of elevated release of adrenal glucocorticoids. Where stress from dieting or exerciser is compounded by physical and/or physiological trauma, the situation is aggravated, causing even higher levels of released cortisol, the principal glucocorticoid that adversely affects the body in elevated levels.

The contributory effect of emotional distress of physical training programs was recognized by Dr. Lewis G. Maharam, in his book, *Maharam's Curve, The Exercise High—How to Get It, How to Keep It*, (W.W. Norton & Co., N.Y. 1992). In a general thesis, Dr. Maharam has correlated the relationship between mood level and effective exercise programs and has devised a useful curve, a truncated sinusoidal with a defined peak, to enable visual programming of the exercise process in conjunction with mood level. The visualized performance curve enables one to manipulate his or her mood level using exercise and following the curve. While cortisol levels were not discussed, the beneficial effect of coordinating mood and exercise using a common sense approach, likely has a corresponding explanation in the level of cortisol release from cumulative non-specific stress.

The devised curve, however, has a universal appeal for defining the concept of strategic event training, where a goal is defined, which may be an athletic contest or the length of a weekend walk, and a definite diet and exercise strategy is devised for peak performance at the time of the event and minimal recovery after the event.

In addition to traditional methods of strategic training, the dietary supplement described herein comprises a powerful tool for optimizing any program of planned diet and exercise.

The intake of appropriate quantities of dietary protein along with non-protein calorie sources, as described in the referenced patent can buffer the destructive effect of elevated cortisol on muscle tissue. Elevated cortisol effectively reduces or blocks amino acid into entry and subsequent conversion to muscle. The use of protein supplements and calorie-dense supplements in above normal quantities permits a change from a catabolic to an anabolic state, minimizing the damaging effect of released cortisol. The ingested protein and carbohydrates are in effect a decoy for the catabolic action of the increased cortisol.

The nutritional supplement, soy derived phosphatidylserine, however, suppresses the release of cortisol under conditions where release would be otherwise increased. This allows available ingested protein to be more available for use by the body in developing muscle and alleviates the antagonistic effect of cortisol on amino acid entry into muscle for the synthesis of new muscle growth.

While the life of primitive man was dominated by brief, intermittent physical stresses, the life of modern man is dominated by chronic mental stress. As a result, our stress arousal system is hopelessly ill-equipped to deal with stress overload, so it overproduces cortisol consistent with a physical exhaustion stage.

For physical stress, the human body is superbly adapted over millions of years for the production of stress hormones. Stress hormones dull pain, redirect energy from nonessential activities, such as digestion or tissue repair, to the specific muscles for fight or flight. But with modern day mental stress, creating a generally elevated background level of cortisol, stress hormones (cortisol) are released in response to physical stress, and are overproduced, and can disrupt digestion, damage the stomach wall, harden arteries, stunt, growth, affect sex life, lower immunity, and promote cancer growth. Excess cortisol has been documented to result in many other physiological and psychological disorders.

Almost any type of physical or mental stress leads to elevated cortisol, which begins by the initial excitation of the hypothalamus. Signals to the hypothalamus come from the hippocampus, limbic system and lower brain stem. After excitation, the hypothalamus produces a corticotrophin releasing factor (CRF). CRF circulates to the pituitary gland where it promotes the secretion of adrenocorticotropic hormone (ACTH), which is quickly followed by a rise in cortisol produced in the adrenal glands. The entire system resulting in cortisol release occurs within minutes after the stress. In summary, CRF→ACTH→Cortisol. Cortisol (Hydrocortisone, 17-hydroxy corticosteroid, 17 OHCS) is the primary stress hormone, the principal feature of the body's stress response. Technically, cortisol is a member of a group of hormones termed corticosterbids or corticoids. Of these, cortisol produces 95% of the effects of corticoids, and is generally referred to as the stress hormone.

The raw material for cortisol production is mainly cholesterol, accounting for 80% of the total cortisol production, the remaining 20% being synthesized by the adrenal cortex. The adrenal glands weigh about 4 grams and lie at the top of each kidney. Each adrenal gland is composed of two parts. The adrenal cortex portion secretes the corticoids, including cortisol.

In the past, athletes and bodybuilders have relied on synthetic anabolic steroids for suppressing cortisol effects enhancing muscle mass and performance, and exerting an overall anti-catabolic effect. Anabolic steroids have well documented, dangerous side effects and are generally banned for athletes performing in most sanctioned athletic events.

Other cortisol suppressors include cimetidine, phenytoin-dilantin, lidocaine, procaine salicylates and the controversial abortion drug RU-486. These drugs in general have adverse side effects that make them unacceptable as a general nutritional supplement for improving health and well-being. Where a nutritional supplement is voluntarily included in a dietary or physical training program, the substance must be both beneficial and physiologically safe, without adverse side effects when taken in often uncontrolled circumstances and in quantities often exceeding recommended levels.

Medical studies in Italy, reported in *Neuroendocrinology*, (1990) 52:243–248 and in the *European Journal of Clinical Pharmacology*, (1992) 42:385–388 by Monteleone, et al have indicated that brain cortex-derived phosphatidylserine (BDPS) administered above threshold amounts suppressed elevation of cortisol levels during and after exercise.

Recently, phosphatidylserine has been extracted from plants, and in particular from soybeans during the production of soy lecithin. The soy-derived phosphatidylserine (SDPS) has clinically the same properties as the, prohibitively expensive, brain-cortex derived phosphatidylserine (BDPS) in its anti-catabolic effect.

As a natural food supplement, SDPS suppresses the elevation of cortisol resulting from stress. Where stress is self-induced as in physical training and dieting, ingestion of SDPS inhibits the detrimental process of protein catabolism, allowing retention of acquired muscle mass and synthesis of ingested protein.

The naturally derived supplement, SDPS, when used in a regimen for self induced physical stress resolves the problems of cortisol suppression using anabolic steroids or other dangerous drugs for muscle retention or amplification. Instead of adverse collateral effects, the supplement enhances the immune system and has other beneficial results for improved health.

The dietary supplement and regimen described primarily devised to promote human health and fitness. It is to be understood that the system is also directed at administering SDPS to animals, particularly performance animals such as sled, racing, show and guard dogs, and for veterinary use in improving the performance of horses in racing, draft or show conditions. The use of SDPS in association with a training program for animals or humans enables ingestion to be timed and correlated with the level of induced physical stress from dieting or exercise to minimize the deleterious effect of cortisol release on body protein and vitalization of ingested protein.

SUMMARY OF THE INVENTION

This invention relates to a naturally derived food supplement for use as an anti-catabolic in a health and fitness regimen. In particular, the dietary supplement is a soybean derived, phosphatidylserine (SDPS), a phospholipid that is a byproduct of soy lecithin production. SDPS is a safe, healthy food supplement that promotes muscle development or retention in exercise and dieting programs where induced stress generates elevated levels of protein consuming glucocbrticoids, in particular cortisol.

Modern fitness programs include exercise as a key to general good health and wellness. In dieting, exercise levels are generally moderate to maintain muscle while losing fat. In physical training, exercise levels are high and for specialty training such as programs for professional athletes and body builders, the level of exercise commonly recommended results in physical trauma. The deleterious physiological effects of dieting or fitness training can be buffered by the ingestion of soy derived phosphatidylserine (SDPS), which suppresses the damaging release of excess levels of cortisol. The use of SDPS to suppress the release of excess cortisol from induced physical stress has no effect on the normal levels of cortisol released during quiescent periods. Cortisol release is thereby controlled to allow cortisol to perform its normal functions in the body's metabolism.

The sequence in triggering cortisol release is rapid and quickly follows the stress stimulus. Where physical stress is deliberately induced, the user of SDPS is able to control the ingestion of SDPS and regulate the timing and quantity according to the regime adopted for the objectives desired. Because the type of physiological stress that induces elevated cortisol release is non-specific, the soy derived supplement is effective in both dieting and exercise programs and in combination programs of regulated diet for weight loss and exercise for lean muscle gain. The controlled effect can be enhanced by the contemporaneous ingestion of carbohydrates and protein, including high grade protein supplements, particularly where increased muscle mass is desired. In this respect, maintenance of an anabolic state is desired and use of my prior invention of an anabolic/ catabolic test kit is advantageous. The use of SDPS increases the intake of expensive dietary amino acids which cortisol inhibits.

Because the user or trainer (for example, where performance animals are concerned) has control over the fitness program, the timing and quantity of administered SDPS can be controlled. This application seeks to teach the optimum levels and timing of SDPS ingestion for typical situations of induced physical stress. Extrapolation from the recommended guidelines allows safe, effective use of SDPS for other similar regimes where health and fitness are the objective.

These and other features of the nutritional supplement system are described in detail in the Detailed Description of the Preferred Embodiments of this specification.

BRIEF DESCRIPTION OF THE DRAWINGS

FIG. 1 is a chart of quantity guidelines for the use of the anti-catabolic supplement, SDPS.

DETAILED DESCRIPTION OF THE PREFERRED EMBODIMENTS

The invention relates to an anti-catabolic dietary supplement, soy derived phosphatidylserine, and in addition, to a regimen for use of soy derived phosphatidylserine (SDPS) to inhibit protein catabolism. SDPS is a phospholipid currently produced as a byproduct of soy lecithin. Soy derived phosphatidylserine (SDPS) is a natural substance that is safe and beneficial for suppressing production of elevated and toxic levels of the stress hormone cortisol. The system herein described provides a regimen for administering SDPS in conjunction with dietary and fitness programs where it is desired to inhibit muscle loss or promote muscle gain for health and fitness.

Phosphatidylserine is a natural substance that when administered orally has been proven to be highly effective at lowering cortisol levels by blunting the hypothalamus reaction to stress. Medical studies using phosphatidylserine derived from animal brain has shown the substance to be effective for a variety of stress factors that elevate cortisol release to physiologically damaging levels.

Naturally occurring in plants, phosphatidylserine has recently been extracted in commercial quantities from soybean. Soy derived phosphatidylserine, SDPS, manufactured for human consumption by Lucas Meyer is extracted as a soybean fractionate in the production of soy lecithin. The resulting yield consists of approximately 97% acetone insolubles. The extracted powder begins at approximately 50% SDPS concentration and is then preferably mixed with lecithin or other beneficial nutrients for easier dispersion and handling. The resulting nutty-tasting power is easily and innocuously blended into foods, drinks, other nutritional supplements or pressed into pills or contained in gel capsules or other delivery products. Ingestion through avenues other than oral are available, such as through suppositories or nasal sprays or liposomes, particularly where oral administration is not possible.

Under dieting and exercise conditions, SDPS is administered at phosphatidylserine levels for suppressing elevation in the level of cortisol release resulting from induced physical stress. SDPS is one of a variety of substances that have been identified as cortisol antagonists. As previously noted, most of the identified substances are not suitable as a dietary supplement to promote health. Where anti-catabolic effects are desired, cortisol antagonists such as anabolic steroids are effective, but have serious, damaging side effects and are not suitable as a healthy dietary supplement.

SDPS, on the other hand, is a naturally derived substance that appears to have beneficial rather than detrimental collateral effects when used as dietary supplements in health and fitness programs. The substance promotes synthesis of ingested protein and inhibits the destructive metabolism of muscle tissue, the body's protein storehouse.

As in my referenced U.S. Pat. No. 5,260,219, a dietary program must be sufficiently flexible to include the circumstance of caloric restriction, where weight loss is desired, and high caloric ingestion, where weight gain or at least gain in muscle mass is desired. In both situations, the induced physical stress will ordinarily cause a dramatic increase in the level of cortisol in the body system, which results in consumption of body protein and a catabolic state.

Ingestion of SDPS interferes with the mechanism leading to stress induced cortisol release, reducing levels by 30% or more. The directional tendency toward a catabolic state is blunted allowing the body to preserve lean muscle mass and burn alternate carbohydrates and fats for fuel. When supplemental amino acids are ingested during periods of suppressed cortisol levels, protein synthesis is not blocked and the body is able to add muscle mass.

The use of SDPS, is a powerful weapon in the fight for good health and fitness. The user or trainer is now able to consciously tailor a dietary and exercise program for optimized results. A dietary restriction of food intake is interpreted as the physical stress of starvation. When restricted diet is combined with exercise the induced physical stress is cumulative. Psychological stress adds to the cumulative level of stress. Therefore, a diet of reduced caloric ingestion with light exercise, requires less SDPS in a daily supplement than the same diet with heavy exercise.

By lowering cortisol production, SDPS reverses many of the toxic, catabolic (muscle wasting) effects that occur from the stress of serious physical training. Generally, cortisol elevation takes between 5–20 minutes after the onset of exercise. Increases in cortisol levels are associated with the training factors of intensity, volume, duration and frequency. After workouts, cortisol may stay elevated, and in the case of chronic training, remain elevated for long periods. Chronic workouts, more than 3 times per week, or workouts of more than 1.5 hours per day, are consistent with elevated cortisol levels. Even more, recreational athletes can elevate cortisol to toxic levels.

SDPS can be seen as an anti-stress nutrient that serves a metabolic balancing or normalizing function, naturally working against the over-production of cortisol.

Cortisol breaks down muscle tissue, while also halting protein (muscle) synthesis. This dual catabolic action not only decreases muscle mass, but robs muscle cells of vital components: water, potassium, creatine, nitrogen. The loss of these substances decrease physical performance and slows recovery. SDPS reverses this, and thereby preserves existing muscle, and enables new protein synthesis to occur with the benefit of utilizing more dietary protein for protein synthesis, with less lost or used for energy.

Cortisol is antagonistic to the uptake of dietary protein, and inhibits the utilization. Instead, dietary protein ingested by athletes via shakes, meat, etc. is shuttled to the liver where it is converted into glucose in the process of gluconeogenesis. This diverts expensive dietary protein from its main task of protein synthesis, tissue repair and growth to an inefficient energy source. SDPS enables dietary protein eaten by the athlete to be more likely taken up by muscle cells and utilized.

Cortisol reduces glucose utilization by muscle cells, creating abnormally high blood glucose, a condition termed "adrenal diabetics". Increasing glucose utilization by taking SDPS means greater muscle energy for physical work performance, and greater glycogen synthesis in muscle and liver after workouts, another key factor to physical performance and enhanced nitrogen balance, an index of the body's protein status.

The above factors lead to less muscle damage from workouts, faster muscle repair, less free radicals, regeneration of carbohydrate (glycogen) and creatine stores.

SDPS helps enhance performance two ways. First it leaves the athlete much more recovered and ready for the next performance. Greater nutritional reserves, especially glycogen and nitrogen balance, help extend performance. Higher glycogen stores alone can increase performance by 30% or more on successive days of training.

Second, the generalized anabolic metabolism via SDPS is strongly associated with greater performance. Reduced lactic acid accumulation and greater cell voluminizing of critical substances are just two factors improved.

Additionally, by protecting lean body mass from catabolic attack by cortisol, SDPS helps to maintain or enhance functional muscle tissue mass which is directly associated with performance.

Although ingestion of SDPS in amounts substantially greater than required for cortisol suppression does not appear to adversely affect health, the supplement is nevertheless moderately expensive requiring control for cost effective administration.

Referring to FIG. 1, a chart for typical SDPS intake protocol is shown with SDPS quantified in milligrams per day. Ordinarily as noted, ingestion of SDPS will be in a mixture with other nutritional supplements or fluids for enhanced effect.

As shown, maintenance of general health and wellness for an individual less than 200 lbs, 100 mg/day is recommended as a baseline quantity where there is no psychological stress and an absence of induced physical stress from dieting or exercise. With dieting the amount of SDPS doubles to 200 mg/day. If dieting for the under 200 lb individual is combined with exercise, the daily amount is increased to 300 mg/day, and with heavy workouts to 400 mg/day. When dieting is combined with extra emotional stress, up to 550 mg/day may be beneficially taken. As shown by the chart, the amount recommend generally correlates with the weight of a person and the level of cumulative stress.

Where an intense physical training program is about to be undertaken, the program is best preceded by a high load level of up to 800 mg/day to infuse SDPS into the cellular system before triggering the cortisol reaction by the induced stress of intense physical training.

High levels of ingested SDPS do not appear to produce toxic results (rats tested at a dose of 2000/mg/kg weight showed no toxic effects). However, at this time, there does not appear to be any justification to exceed 800 mg/day level for human ingestion to achieve the objectives here described. As noted, the regimens specified in part are devised for efficient use of specialty supplements that may be expensive, and cost is therefore an important consideration.

It is to be understood that the chart of FIG. 1 provides a general guide to correlate the activity of the individual with the recommended daily intake for positive results.

As previously mentioned, use of SDPS as a anti-catabolic dietary supplement is best integrated into a dietary program with other nutritional substances depending in part on the goal. Three typical regimes are described as follows for dieting, aerobic training, and weight training:

Fat Loss (Dieting)

Here the goal is to lose body fat while retaining lean body mass, a program that is usually very difficult.

- Calories 1500–2000/day
- Low fat, high complex carbohydrates fibrous, sufficient protein (0.25 to 1 gram/lb. bodyweight.)
- Light aerobics 4–7 days a week or light weight workouts to help preserve lean body mass.
- 4 small meals with water.
- Vitamin-mineral supplement.

SDPS intake of 100–300 mg/day. Here, the less intake of calories, the more SDPS is required.

Aerobic Endurance (Bicycle, Running, Swimming)

The goal is lean muscle and high endurance, and is characterized by long, slow distance training using primarily aerobic energy pathways.

- 3–5 workouts 30–60 minutes each, 50–85% Vo2 maximum heart rate, bike, run and swim to reduce biomechanical damage.
- 3–5 meals per day emphasizing carbohydrate and protein intake (0.2 to 0.75 grams/lb bodyweight.)
- Sports drink during workout.
- 8 glasses of water to combat dehydration.
- Very high carbohydrate intake for endurance events.
- Intake of SDPS helps reduce hyper cortisol syndrome, common in endurance athletes.

Start with SDPS at 100 mgs, and when training intensity reaches 50% or more, increase to 400–800 mgs/day. During two a day workouts, take before hardest workout.

Weight/Muscle Gain

Here, the key is to convert high calorie/protein intake into lean body mass while minimizing body fat gains.

- Systematic resistance training with weights or other apparatus with the goal of muscle hypertrophy via muscle fiber stimulation, amino acid (protein) uptake and protein synthesis.
- 4–7 meals per day.
- Frequent sports drink rich in carbohydrate during workouts.
- 2,000 to 7,500 calories per day.
- Protein intake from 0.2 to 1 gram per lb of body weight, typically using dietary supplement in the form of milk protein/amino acids including whey, egg, turkey breast jerky, etc.
- 3–5 workouts per week.
- Multi body parts, or split routines emphasis upper and lower body, push pull antagonistic muscles, or similar split routines.
- Aerobics now common, usually with stationary bikes or stairmasters, 10–30 minutes after workouts or non workout days. The weight/muscle gain regime increases cortisol stimulation greatly around the clock.

SDPS loading cycle, 1 hour before workouts, take 400–800 element SDPS during loading phases, and 100–250 mg during maintenance phases of low intensity. In off season, cease intake or reduce to base line level of 100 mg or less per day. One or two a day workouts take before hardest workout. Take in PM prior to bed if very high workload.

In general, ingestion of modest amounts of carbohydrates and SDPS should precede physical workouts for energy and reduced cortisol release, and protein supplements should follow workouts for recovery and development of lean body mass. Fluids should be taken at all times to avoid dehydration and improve circulation of body fluids.

In summary, in any health or fitness program where the goal is improved performance, diet and exercise can be deliberately planned for optimized conditioning. In planned health and fitness programs the level of induced physical stress from diet or workout can generally be predicted. With any additional psychological stress considered cumulative, the total level of stress can be approximated and used as a guideline for adjusting the daily intake of SDPS. It is to be understood that the strategy for programming intake of SDPS is dynamic and may change from day to day depending on planned daily events and long-term performance and conditioning goals.

In planning an exercise and diet program, the concept of strategic event training is predicated on a short term or long term performance goal, i.e., the event. The body at the time of the event is conditioned for optimum performance. It is expected that after the event there is a period of recovery. This cycle mirrors the Maharam curve which is a useful tool for planning or programming the regimen. As noted, the goal can be short-term, i.e., a good workout session, longer term, i.e., loss of 15 lbs. in a month, or the basic life-time plan of increased longevity. Since improving longevity as a physically fit specimen is the ultimate goal, any health and fitness program should avoid excesses or dietary supplements that may be helpful in the short run, but are harmful in the long run.

The dietary supplement SDPS is a remarkably safe and beneficial nutrient for use in any health and fitness program where anti-catabolic effects are desired.

While, in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A muscle development, diet supplement comprising a composition including a plant derived phospholipid concentrate having at least 100 mg of phosphatidylserine, wherein at least half of the phospholipid concentrate is phosphatidylserine; and, a protein supplement in a physiologically beneficial amount.

2. The diet supplement of claim 1, wherein the plant is soy.

3. An anti-catabolic dietary composition comprising a soy derived phospholipid concentrate having at least 100 mg of phosphatidylserine wherein at least half of the phospholipid concentrate is phosphatidylserine; and, a physiologically beneficial amount of a protein supplement.

4. The anti-catabolic dietary composition of claim 3, wherein the plant is soy.

5. A nutritional and physical fitness regimen for optimizing lean muscle development comprising the step of ingesting at least a physiologically effective amount of an anti-catabolic dietary nutrient, wherein the nutrient is a soy derived phospholipid concentrate having at least 100 mg of phosphatidylserine therein and wherein at least half of the phospholipid concentrate is phosphatidylserine, and inducing physical stress by performing physical exercise.

6. The regimen of claim 5 wherein the amount of phosphatidylserine ingested is at least 200 mg/day.

7. The regimen of claim 5 wherein the amount of phosphatidylserine ingested is less than 800 mg/day.

8. The nutritional and physical fitness regimen of claim 5 including the added step of ingesting a protein supplement in a physiologically beneficial amount, contemporaneously with the step of ingesting the anti-catabolic dietary supplement.

* * * * *